United States Patent [19]

Scheller et al.

[11] Patent Number: 4,837,857
[45] Date of Patent: Jun. 6, 1989

[54] FOOT PEDAL ASSEMBLY FOR OPHTHALMIC SURGICAL INSTRUMENT

[75] Inventors: Gregg D. Scheller; Jerry S. Gahn, both of Ballwin; Daniel E. Higgins, St. Louis; Richard Wendt, Des Peres; James Gibeltirra, Florissant; J. Alan Ritter, Des Peres, all of Mo.

[73] Assignee: Storz Instrument Company, St. Louis, Mo.

[21] Appl. No.: 927,807

[22] Filed: Nov. 6, 1986

[51] Int. Cl.$^4$ .............................................. H04B 9/00
[52] U.S. Cl. .................... 455/617; 74/594.1; 128/303.1; 455/603; 370/3; 370/4
[58] Field of Search .............. 455/603, 608, 606, 607, 455/612; 370/3, 4; 250/237 R, 237 G, 231 SE, 465.1; 74/594.1, 594.4; 251/295; 128/303.1

[56] References Cited

U.S. PATENT DOCUMENTS

| | | | |
|---|---|---|---|
| 4,074,808 | 2/1978 | Gillespie et al. | 250/237 R |
| 4,122,853 | 10/1978 | Smith | 128/303.1 |
| 4,263,506 | 4/1981 | Epstein | 250/237 G |
| 4,426,738 | 1/1984 | Sato | 455/603 |
| 4,491,983 | 1/1985 | Pinnow et al. | 370/4 |
| 4,533,830 | 8/1985 | Beauprey | 250/237 R |
| 4,554,917 | 11/1985 | Tagnon | 128/303.1 |
| 4,633,224 | 12/1986 | Gipp et al. | 250/231 SE |
| 4,654,636 | 3/1987 | Rusk | 250/231 SE |
| 4,664,524 | 5/1987 | Hattori et al. | 250/237 G |
| 4,667,098 | 5/1987 | Everett | 250/237 G |

Primary Examiner—Robert L. Griffin
Assistant Examiner—L. Van Beek
Attorney, Agent, or Firm—Harness, Dickey & Pierce

[57] ABSTRACT

A foot pedal assembly for remotely controlling an instrument is disclosed. The foot pedal assembly comprises a base member upon which a foot pedal is mounted. The foot pedal assembly also comprises a means for providing an optical transmitted signal for use in controlling the instrument in response to the movement of the foot pedal. The means for providing an optically transmitted signal comprises a plurality of individual light channels.

25 Claims, 5 Drawing Sheets

FOOT PEDAL ASSEMBLY FOR OPHTHALMIC SURGICAL INSTRUMENT

BACKGROUND AND SUMMARY OF THE INVENTION

The present invention relates generally to microsurgical and ophthalmic systems, and more particularly to a foot pedal assembly for use with a control system for operating microsurgical instruments.

Ophthalmic microsurgical systems provide one or more pneumatically operated (fluid pressure operated) surgical instruments connected to a control console. The control console provides the fluid pressure signals for operating the instruments and usually includes several different types of human actuable controllers for controlling the fluid pressure signals supplied to the surgical instruments. Usually included is a foot pedal assembly which the surgeon can use to control a surgical instrument.

Conventional foot pedal assemblies use a variety of pneumatic and electrical actuators to control microsurgical instruments. In pneumatic foot pedal assemblies, pneumatic fluid enters the foot pedal assembly through an inlet port which is connected to a pneumatic supply. The amount of pneumatic fluid leaving the foot pedal assembly is proportional to the amount of depression on the foot pedal of the assembly. The larger the depression on the foot pedal, the greater the amount of pneumatic fluid which is delivered to the control console from the foot pedal assembly. Foot pedal assemblies which employ electrical actuators use a potentiometer which is attached to the pedal. As the pedal is pivoted by the operator, the resistance of the potentiometer changes. This change in resistance is used by the control console to generate a signal for adjusting the microsurgical instruments.

While conventional foot pedal assemblies have helped to make microsurgery and ophthalmic surgery possible, these assemblies are not without drawbacks. Such foot pedal assemblies often become inoperable when they were exposed to saline, which is used in ophthalmic microsurgical procedures, and therefore were often unreliable over an extended period of time. In addition, because such foot pedal assemblies provided an analog input to the control console, the foot pedal assemblies were not generally capable of providing a high resolution positional signal that would otherwise be possible with a digitally encoded signal. Furthermore, the use of an analog input made it necessary to calibrate each foot pedal to a specific control console. Finally, the cable from the control console to electrically activated foot pedal assemblies often had to be relatively short as the resistance of the cable had to be below a preselected level to comply with certain equipment specifications.

The present invention greatly advances the art by providing a foot pedal assembly which delivers an optically encoded signal to a of microsurgical or ophthalmic system which is responsive to the degree depression of the foot pedal. By optically encoding the degree of depression of the foot pedal, the resolution of the movement of the foot pedal may be adjusted to accommodate a variety of surgical techniques. In addition, the foot pedal is less susceptible of becoming inoperative when it is exposed to saline during surgical procedures. Furthermore, since a digitally encoded input is used, there is no need to calibrate each foot pedal to a specific control console. Finally, since the present invention does not use electrical cables between the foot pedal assemblies and the control console, the cables may be longer than would otherwise be acceptable.

More specifically, the foot pedal assembly according to the present invention is adapted for remotely controlling microsurgical instruments. The foot pedal assembly comprises a base member upon which a foot pedal is mounted. The foot pedal assembly also comprises means for providing an optically transmitted signal for use in controlling the microsurgical instrument in response to the movement of the foot pedal.

In further accordance with the invention, the foot pedal is mounted on one end of the base member for pivotal movement in a general vertical direction. The foot pedal assembly also includes a rotating optical encoder for providing a digitally encoded signal which is optically transmitted to the control console for controlling the microsurgical instrument.

Still further in accordance with the present invention, the optically transmitted signal comprises a plurality of individual light conveying channels. The means for providing an optically transmitted signal may also include an optical fiber conduit for defining each of the light channels and for transmitting light from the base to the plurality of light conveying channels. These fiber optic conduits eliminate the need to supply electricity to the foot pedal, and they also eliminate the need for pressure sensitive pneumatic piping as well. Accordingly, the present invention provides an effective, durable device for conveying signals to the surgical controller.

For a more complete understanding of the invention, its objects and advantages, reference may be made to the following specification and to the accompanying drawings.

BRIEF DESCRIPTION OF THE DRAWINGS

FIG. 3 is a top view of the foot pedal assembly shown in FIG. 1;

DESCRIPTION OF THE PREFERRED EMBODIMENT

Figure 1:
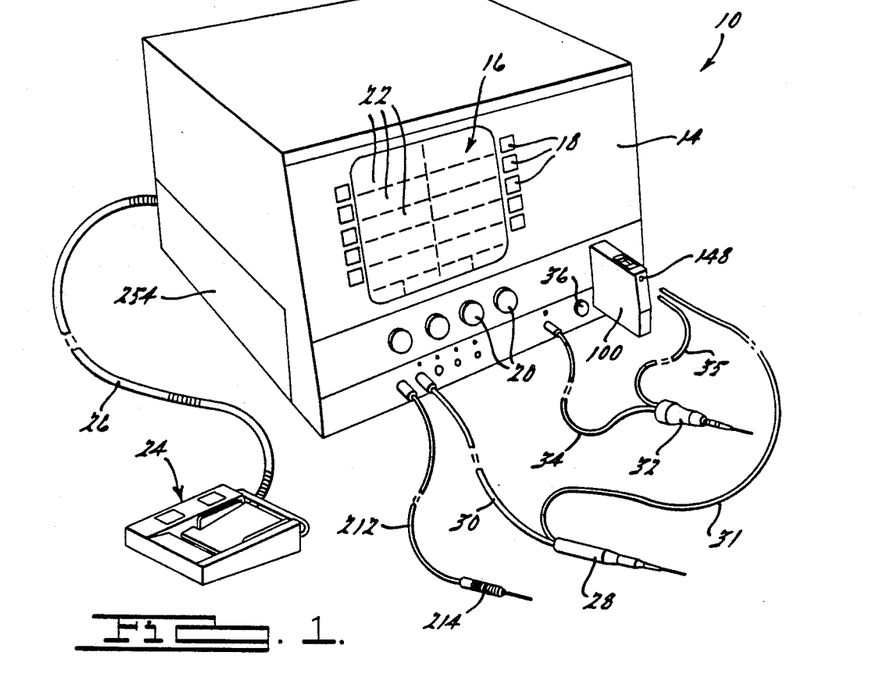
FIG. 1 is a perspective view of the microsurgical control system using the foot pedal assembly of the present invention.
Figure 2:
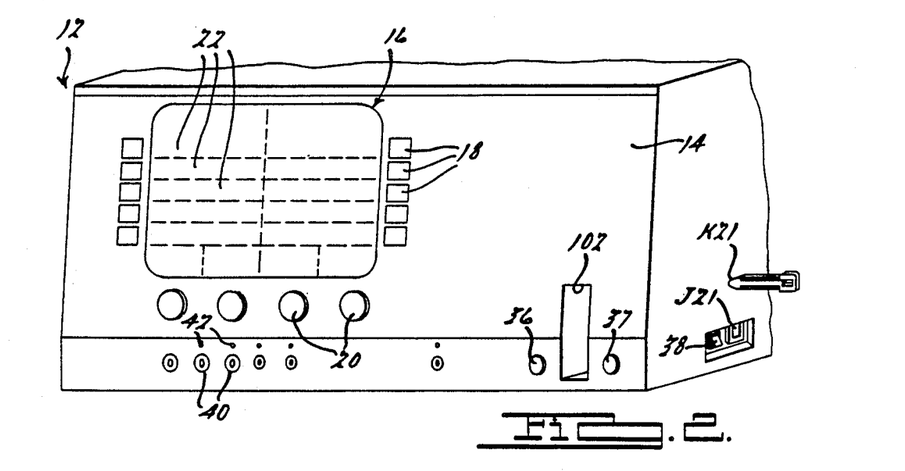
FIG. 2 is a front view of the microsurgical system console shown in FIG. 1.

Referring first to FIGS. 1 and 2, a microsurgical control system 10 is provided having a foot pedal assembly 24 according to the present invention. The control system 10 includes a system console 12 which has an upwardly and inwardly sloping front panel 14 and at least one removable access door 254 in one of the side panels. On the front panel 14 is an electronic display screen 16, a plurality of push button switches or touch sensitive pads 18 and a plurality of "endless" digital potentiometer knobs 20. The push buttons 18 and knobs 20 are actuable operations by the surgeon or nurse to select various different modes of operations and functions used in various surgical procedures.

The console 12 also includes a cassette eject button 36, an irrigation pinch valve 37, and a power on/off switch 38.

The electronic display screen 16 is controlled by a computer to provide one or more different menus or messages which instruct the operator as to the function of the buttons 18 and knobs 20 for the particular mode selected. The display screen 16 may be conceptually divided into display screen regions 22 with the buttons 18 and knobs 20 being positioned at locations around the periphery of the screen 16 corresponding to the regions 22. By virtue of the location of the buttons 18 and knobs 20 adjacent the screen 16, for example, a message in the upper left-hand corner of the screen 16 is readily understood by the operator as referring to the upper left most button. This arrangement allows the indicated function of each button 18 and knob 20 to be readily changed. The use of an electronic display screen 16 also permits the buttons 18 and knobs 20 to be labeled in virtually any language.

The microsurgical control system 10 is adapted for use with a number of different surgical instruments. As shown in FIG. 1, a fiber optic illumination instrument 214 is coupled to the console 12 via fiber optic cable 212. Also illustrated is a fragmentation emulsification instrument 28 coupled to the console 12 through an electrical cable 30. The instrument 28 is also coupled to a collection container or cassette 100 through an aspiration tube 31. A cutting instrument 32 is also shown which is coupled to the console 12 through tubing 34 and to the cassette 100 through tubing 35. The cutting instrument 32 may be a guillotine cutter for vitrectomy procedures, or it may be a microscissors instrument for proportionate and multiple cutting. However, when the microscissors instrument is used, the instrument is not connected to the cassette 100.

While certain microsurgical instruments have been illustrated in FIG. 1, it will be understood that the microsurgical control system 10 can be used with other similarly equipped instruments. In general, any of the microsurgical instruments are actuated or controlled by fluid pressure (positive pressure or negative pressure). However, it should be appreciated that other suitable types of control signals may be used in the appropriate application.

To provide irrigation/aspiration capabilities, the control system 10 further includes the removable cassette 100 which may be inserted into a cassette slot 102 in the console 12. The cassette 100 has a passageway opening 148 to which an aspiration tube from an aspiration instrument may be connected. The console 12 also includes a plurality of couplers 40 to which surgical instruments described above may be attached. Above each coupler 40 is a light emitting diode 42 which is illuminated when the instrument connected to the associated coupler 40 is activated. To store the operating parameters of a particular microsurgical operation, the control system 10 electrically communicates with a digitally encoded memory key k21. The memory key k21 includes an integrated memory circuit which stores the operating parameters for a particular surgical procedure. The console 12 receives the key K21 through a slot J21. Suitable types of memory keys K21 are commercially manufactured by Data Key Inc., Burnsville, MN. However, it should be appreciated that other suitable means for accessing specifically assigned memory locations may be used in the appropriate application.

A further description of the control system may also be found in the following commonly owned patent applications which were filed on even date herewith, and which are hereby incorporated by reference: Scheller, et al U.S. patent application Ser. No. 928170, entitled "Control System For Ophthalmic Surgical Instruments"; Scheller, et al U.S. patent application Ser. No. 927827, entitled "Illumination System For Fiber Optic Lighting Instruments"; and Scheller U.S. patent application Ser. No. 928265, entitled "Collection Container For Ophthalmic Surgical System".

Referring to FIGS. 3 through 9, a first embodiment of a foot pedal assembly 24 according to the present invention is shown. The foot pedal assembly 24 is used to control different surgical instruments which are connected to microsurgical control system 10. Encoded optical signals propagating through optical fibers in the cable 26 are detected and decoded within the console 12 of the control system 10. The foot pedal assembly 24 includes two side actuators 64 and 66 and a foot pedal actuator 68. By movement of the actuators 64, 66 and 68, an operator is able to deliver optically encoded control signals to the console 12 in the manner described below.

Figure 4A:
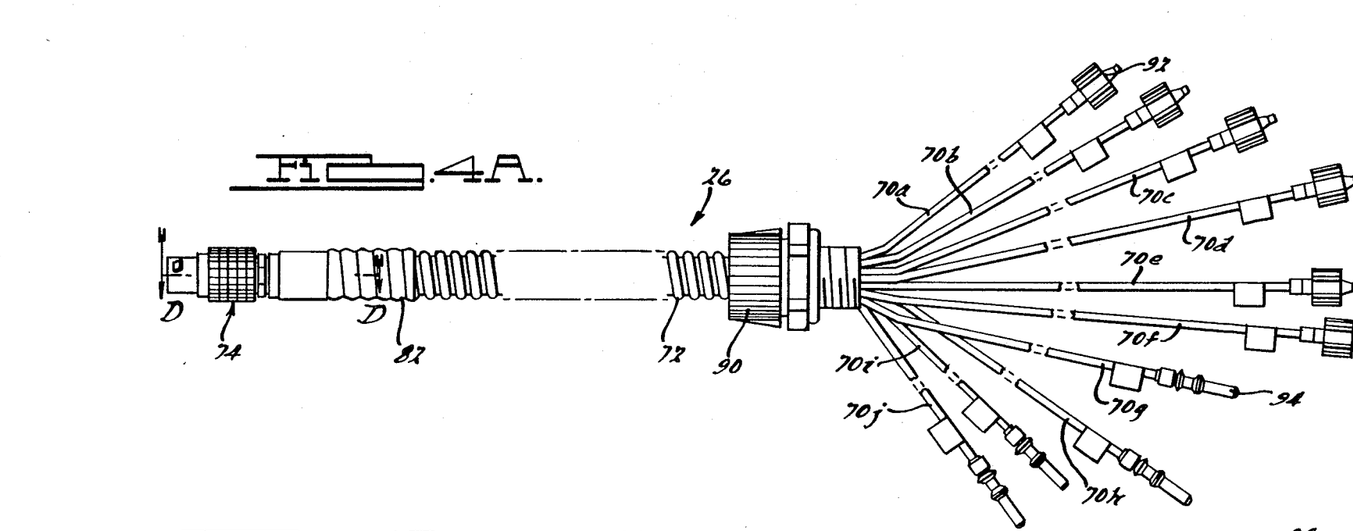
FIG. 4A is a plan view of the cable shown in FIG. 3.

To permit optical communication between the console 12 and the foot pedal assembly 24, the cable 26 generally comprises ten optical channels or fibers 70a–70j which are surrounded by a nonmetallic flexible sheath 72. These optical fibers are shown in FIG. 4A. Five of the optical fibers 70a–70j are used to deliver light from a light source within the console 12 to the foot pedal assembly 24. The remaining five optical fibers are used to carry optically encoded signals from the foot pedal assembly 24 to the system console 12 which indicate the relative position of the actuators 64, 66 and 68.

Figures 4B, 4C:
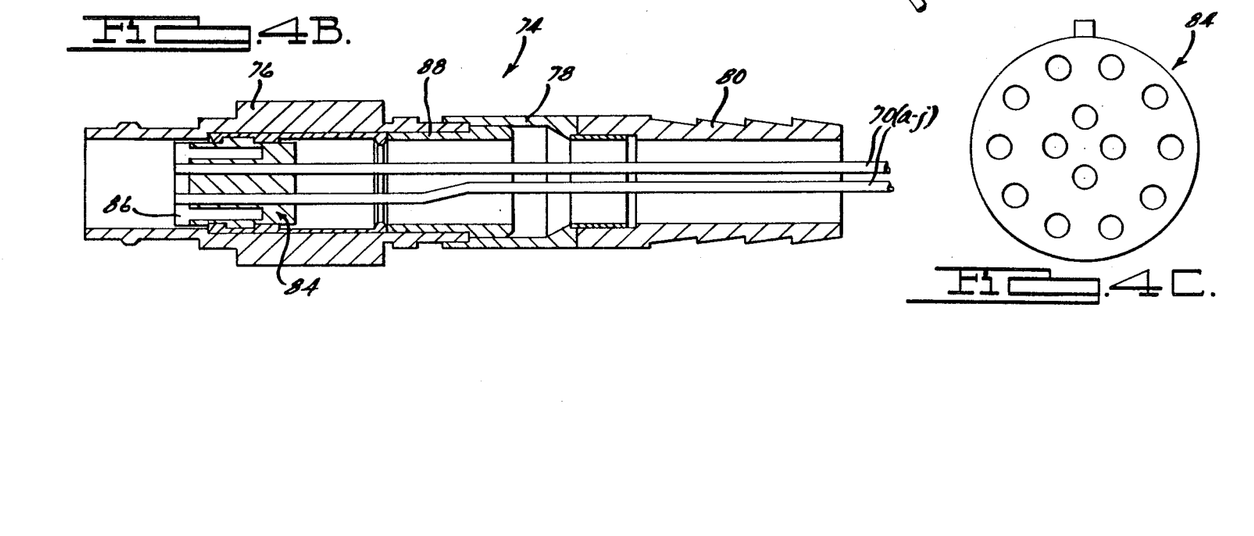
FIG. 4B is a view of the cable taken through line D—D of FIG. 4A.
FIG. 4C is a view of a connector insert used in the cable shown in FIG. 4B.
Figure 5:
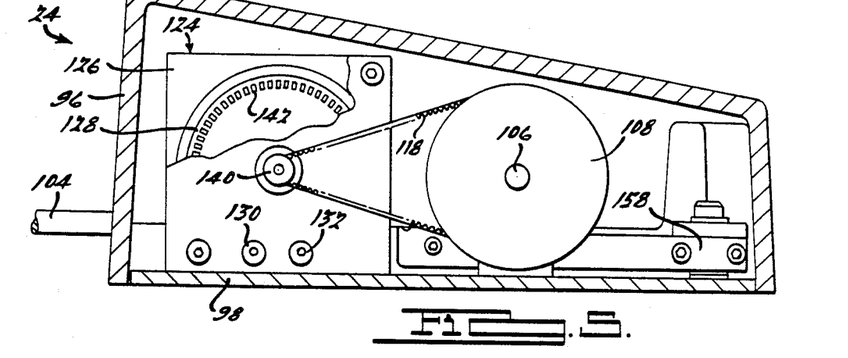
FIG. 5 is a view of the foot pedal assembly taken through line A—A of FIG. 3.
Figure 6:
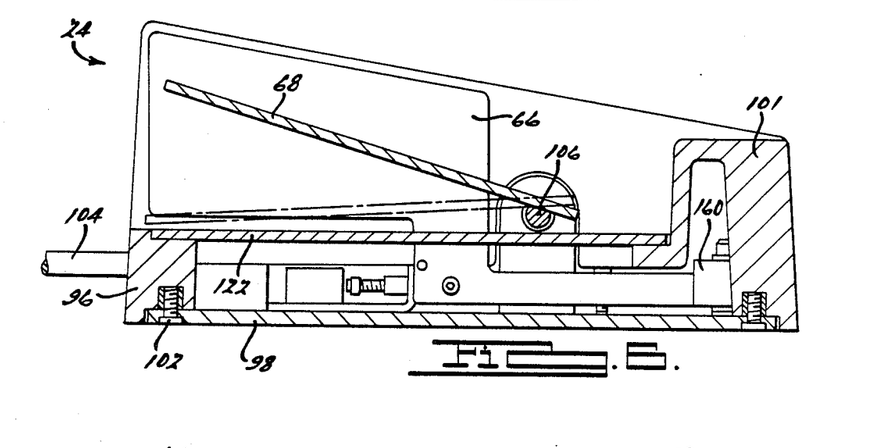
FIG. 6 is a view of the foot pedal taken through line B—B of FIG. 3.
Figure 7:
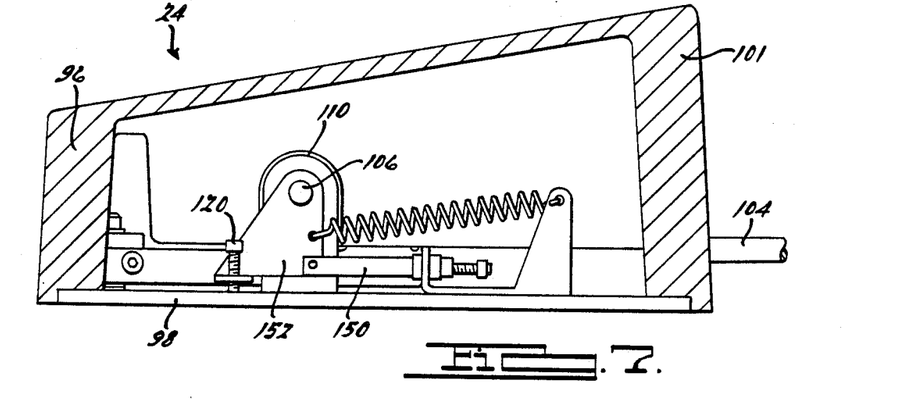
FIG. 7 is a view of the foot pedal assembly taken through line C—C of FIG. 3.

The cable 26 also includes a connector assembly 74 for attaching the cable 26 to the system console 12. FIG. 4B shows a cross-sectional view of the connector assembly 74. The connector assembly includes a connector shell 76 (Lemo part no. FG2B), a back nut 78 which is threaded on the shell 76, and a barbed fitting 80 which is press fitted onto the back nut 78. The sheath 72 is fitted over the barbed end of the fitting 80, on a coaxially disposed shrink tube 82 (Rentek DWP125 ¾ BL) is used to complete the connection between the sheath 72 and the connector assembly 74.

FIG. 4B also illustrates two of the optical fibers 70a–70j extending through the connector assembly 74. The ends of these optical fibers are stripped and glued into an insulating insert 84 with an epoxy. A silastic gasket 86 is also disposed on the forward end of the insert 84. The insert 84 is held in place by a collet assembly 88 (Lemo part nos. FG2B9MM and FG2B) which is coaxially disposed within the shell 76. FIG. 4C shows a rearward view of the insert 84. As illustrated, the insert is formed with a number of spaced holes for separating the optical fibers 70a–70j.

Returning again to FIG. 4A, a strain relief connector 90 (Harvey Hubbel, Inc., Kellems Div. model Polytuff II F2038) is shown at the opposite end of the cable 26. Beyond this connector, the optical fibers 70a–70j extend so that they can be suitably connected to the appropriate components within the foot pedal assembly 28. In one form of the invention these optical fibers are DuPont Crofon 1000 micron core fiber optic cables. However, as with each of the components being described, other suitable substitutes may be used in the appropriate application. Each of the optical fibers 70a–70j is provided with an optical connector to facilitate assembly to the foot pedal assembly 28. Specifically, optical fibers 70a–70f are provided with a connector 92 (AMP 227686-1, 861403-7 and 861403-7) for permitting a threaded connection, while optical fibers 70g–70j are provided with a connector 94 (Hewlitt Packard HFBR-4501/4511) for permitting a snap-fit connection.

To provide support for the foot pedal actuator 68, a housing 96 is provided. The housing 96 is attached to a base member 98 which is integrally connected to the housing through a plurality of screws 120. While the housing 96 may be fabricated from polyurethane structural foam, other suitable materials such as aluminum, other plastic materials, etc., may be used. A handle 104 is provided which is attached to the upper member 101 so that the foot pedal assembly can be easily carried by the operator. While the handle 104 may be fabricated from anodized aluminum, it is to be understood that other suitable materials may be used.

To allow movement of the foot pedal actuator 68 to be optically encoded, the foot pedal actuator 68 mechanically communicates with an axial member 106 which drives a toothed timing pulley member 108. The axial member 106 is supported by the projections 110 and 112 which are secured to the base member 98. Two bushings 114 and 116 are provided on the projections 110 and 112 to permit free rotation of the axial member 106. The gear member 108 is used to drive a timing belt 118 which mechanically communicates with a rotary optical encoder described below. The maximum upward position of the foot pedal actuator 68 is limited by a stop screw 120, while the maximum downward position of the pedal is limited by a plate member 122. By locating the stop screw 120 and the plate member 122 as described above, the preferred pedal angular displacement may be selected to be about 20 degrees. It is to be understood, however, that other suitable displacements may be used as well.

To indicate the angular position of the foot pedal actuator 68, a rotary optical encoder 124 is provided. The rotary optical encoder 124 comprises an encoder housing 126 and an optical encoder disk 128. The disk 128 is supported for rotational movement by ball bearings 129. The optical transmitter cable connectors 130 and 132 optically terminate optical fibers 70g and 70h, while the optical receiver cable connectors 134 and 136 optically terminate the optical fibers 70i and 70j. The optical encoder disk 128 includes an axial projection 138 which communicates with a gear member 140. the gear member 140 is driven by the timing belt 118 so as to cause rotation of the disk 128 upon rotation of the gear member 108 by the foot pedal actuator 68. It should be noted that the pulley 108 and encoder 124 are positioned off to the side of the foot pedal actuator 68. This fact coupled with the relative sizes of the pulley 108 and gear 140 enable a very high resolution to be achieved.

Figure 8:
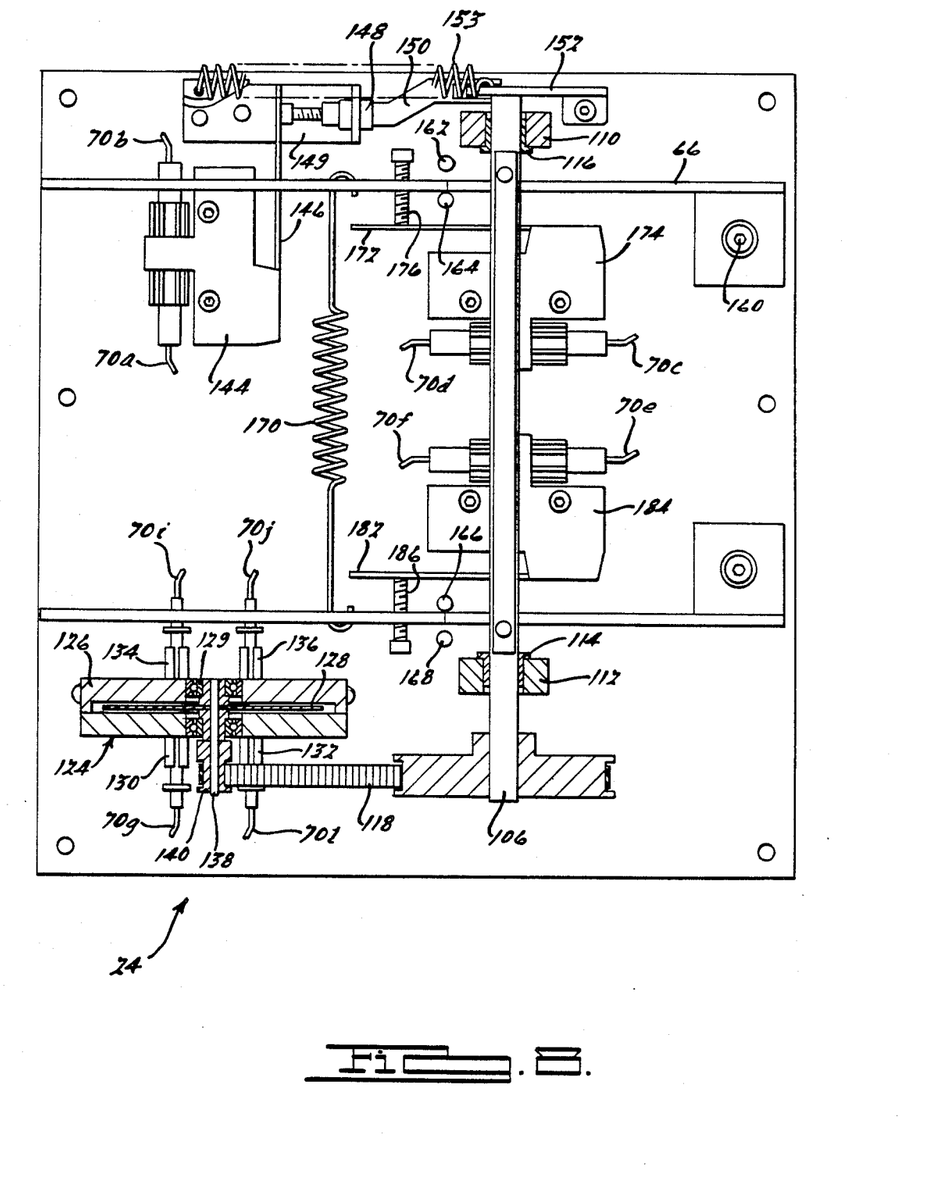
FIG. 8 is a plan view of the foot pedal assembly with the housing removed.
Figure 9:
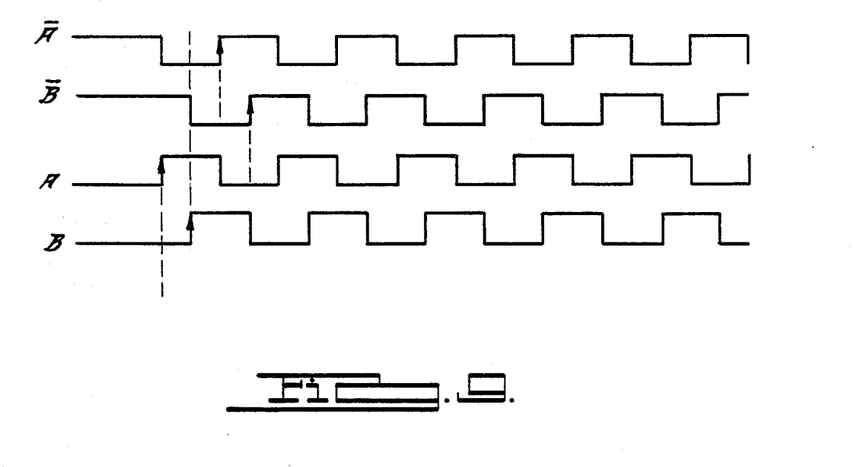
FIG. 9 is the output from two optical fibers which carry the optical signals indicating the degree of pedal depression.
Figure 10:
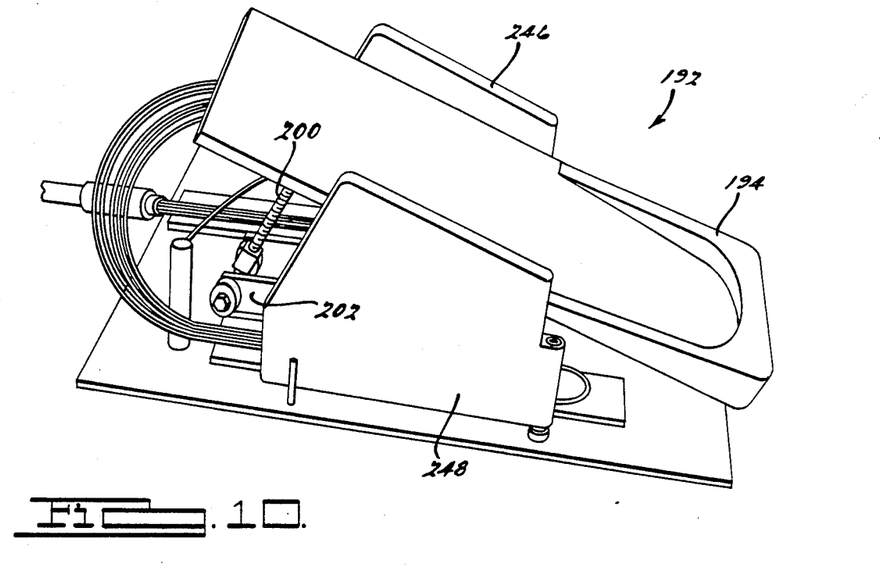
FIG. 10 is a perspective view of an alternative embodiment of the foot pedal assembly according to the present invention.
Figures 11, 12, 13:
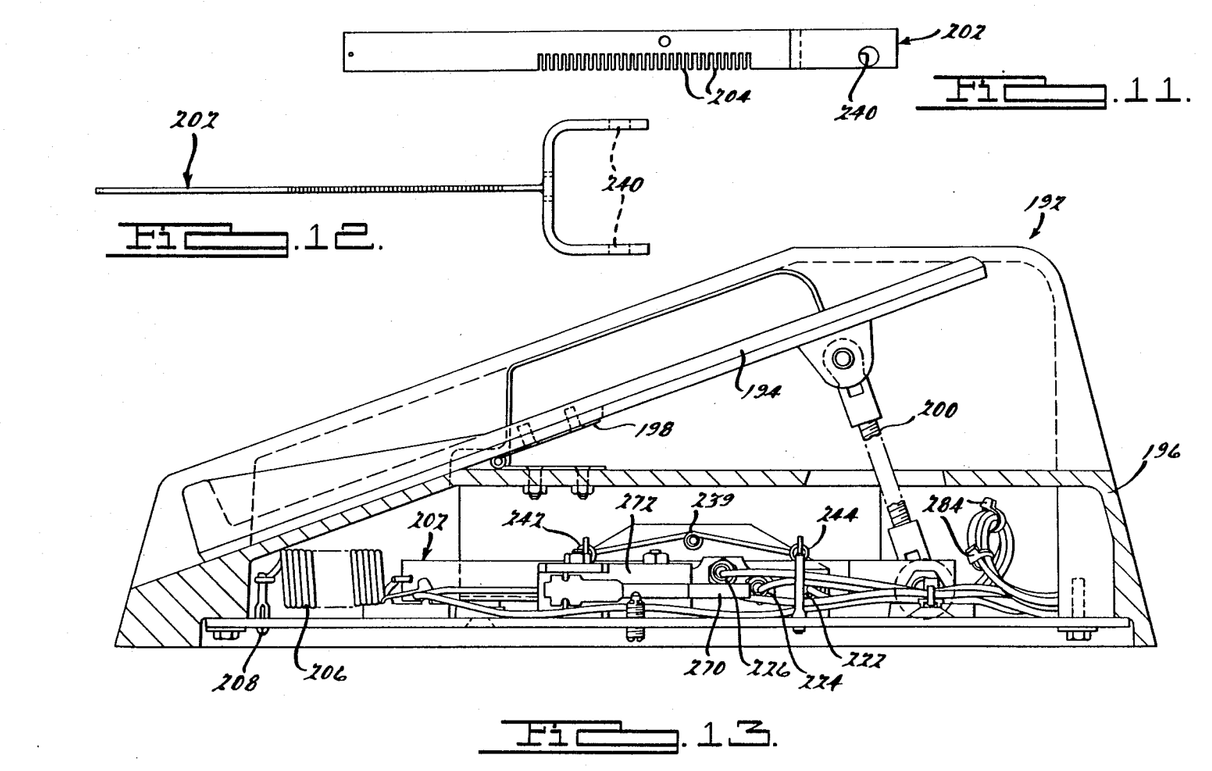
FIGS. 11 and 12 show two views of the linear optical encoder used with the foot pedal assembly shown in FIG. 10.
FIG. 13 is a side elevation view of the foot pedal assembly of FIG. 10 shown partically in cross-section.
Figure 14:
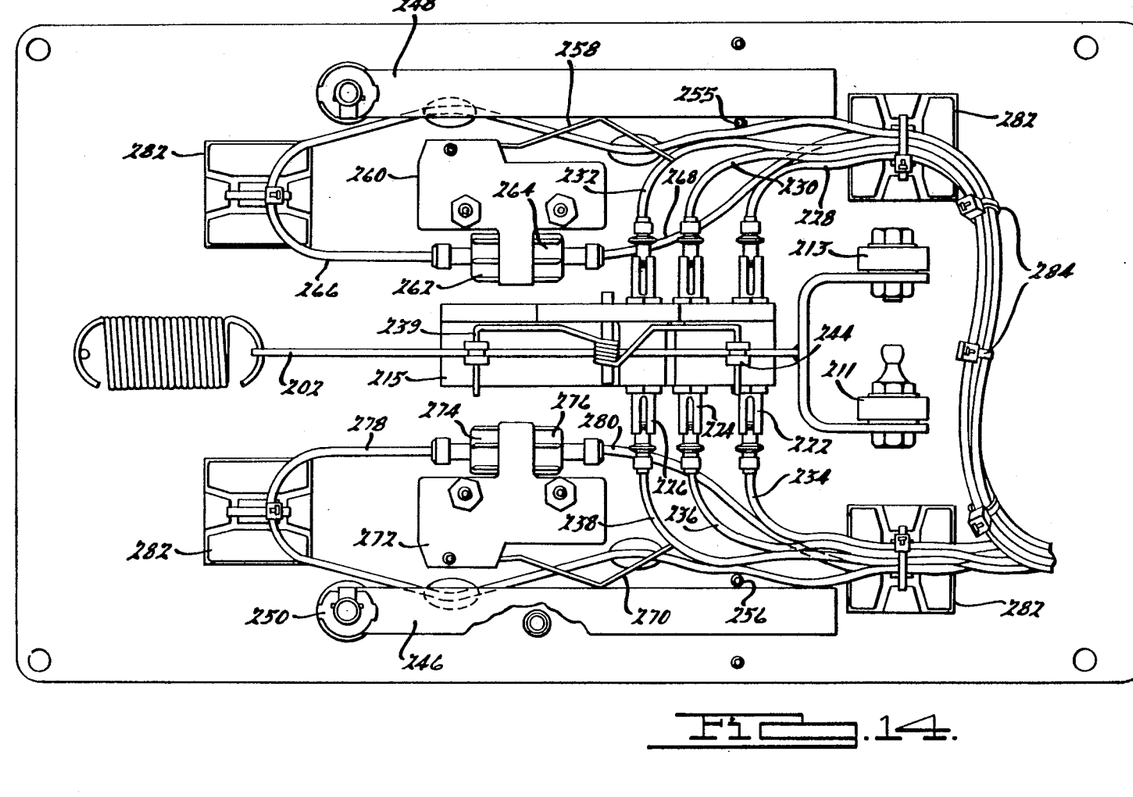
FIG. 14 is a plan view of the foot pedal assembly shown in FIG. 12 with the pedal removed.

The rotary optical encoder 124 permits selective communication between the two optical transmitter cable connectors 130 and 132 and their respective optical receiver cable connectors 134 and 136 through the slots 142 in the encoder disk 128. The optical receiver cable connectors 134 and 136 and their respective optical transmitter cable connectors 130 and 132 are located in such a manner as to produce square wave signals which are 90 electrical degrees out of phase. By locating the optical receiver cable connectors 134 and 136 and optical transmitter cable connectors 130 and 132 in this manner, the output to the optical receivers 134 and 136 may be used to generate a reflected or Gray code representation of the rotary displacement of the disk 128. As shown in FIG. 8, the outputs A and B from the respective fibers 70g and 70h are initially low indicating that light is prohibited from passing from fibers 70i and 70j to fibers 70g and 70h due to the relative location of the optical encoder disk 128. An angular displacement of the encoder disk 128 allows light to pass between the fiber 70g and the fiber 70i through one of the slots 142, thereby producing an output A through the fiber 70g. If the encoder disk 128 is further angularly displaced, the output B from the fiber 70h goes high. Further angular displacement of the encoder disk 128 causes the output A to go low while the output B remains high. If the encoder disk 128 is further displaced, the position of the encoder disk 128 prohibits light from the fibers 70g and 70h to be received by the fibers 70i and 70j, thereby driving both outputs A and B low. Because the output from the optical fibers 70g and 70h may be digitally decoded by the console 12, the console 12 can adjust the response of the foot pedal assembly 24.

To provide a signal indicative of the maximum upward position of the foot pedal actuator 68, an upper limit switch 144 is provided. The switch 143 is connected to the optical fibers 70a and 70b via their respective connectors 92. The upper limit switch 144 includes a lever portion 146 which mechanically communicates with a switch actuator 150. The actuator 150 is adapted to slide through a Teflon bushing 148 which is disposed in a bracket 149. The switch actuator 150 is connected to a rotational member 152 which is attached to the axial member 106. The rotational member 152 is also connected to a foot pedal return spring 153 which extends between the member 152 and the bracket 149. Upon displacement of the foot pedal actuator 68, the lever 150 of the upper limit switch 144 permits optical coupling between the optical fibers 70a and 70b. When such optical communication occurs, the optical signal delivered by the optical fiber 70b to the console 12 is used to indicate that the foot pedal 68 actuator is in its upwardmost position.

To permit lateral movement to actuate the foot pedal assembly 24, the foot pedal assembly 24 further comprises two side actuators 64 and 66. The side actuators 64 and 66 are mounted to the base 98 by pivot mounts 158 and 160. Lateral movement of each of the side actuators 64 and 66 are limited by the stops 162–168 and are biased against the stops 164 and 166 by a return spring 170. To permit lateral movement of the side actuator 66 to be optically encoded, the side actuator 66 mechanically communicates with the lever portion 172 of a side actuator switch 174 through an adjustment screw 176. The side actuator switch 174 is connected to the optical fibers 70c and 70d. Movement of the side actuator switch 174 thereby displaces the lever portion 172 of the side actuator switch 174 so as to permit optical coupling between an optical fiber 70c and the optical fiber 70d. Lateral movement of the side actuator 66 thereby causes an optical signal to be received by the optical fiber 70c and delivered to the console 12. Similarly, the side activator 64 also mechanically communicates with the lever portion 182 of a side actuator switch 184 through an adjustment screw 186. The side actuator switch 184 is connected to the optical fibers 70e and 70f. By lateral displacement of the side actuator 64, the side actuator switch 184 permits optical coupling between the optical fiber 70e and optical fiber 70f. The optical fiber 70f therefore transmits an optical signal to the console 12 when the side actuator 64 is displaced.

Referring again to FIG. 3, the housing 96 is preferably provided with printing which indicates the functions of the foot pedal 68 and the two side actuators 64–66 during different surgical procedures. In this regard, it should be appreciated that the variability of the foot pedal assembly 24 is one of the significant advantages of the present invention. With the digital encoding, the control console 12 can define and redefine the functions of the foot pedal 68 and side actuators 64–66. Thus, for example, the foot pedal 68 could be used to control the scissors in the "Posterior" mode; whereas, in the "Anterior" mode, the foot pedal could be used to control irrigation.

A further embodiment of the present invention is shown in FIGS. 10–14. In this embodiment, the foot pedal assembly 192 includes a foot pedal actuator 194 which is pivotally connected to the housing 196 of the assembly 192 by a hinge 198. The foot pedal actuator 194 mechanically communicates with a vertical support member 200 which in turn is connected to a linear optical encoder 202. The vertical support member 200 is used to linearly displace the linear optical encoder 202 upon depression of the foot pedal 194. The linear optical encoder 202 includes a plurality of generally parallel slots 204 which are used to generate a digitally encoded optical signal as described below. To upwardly bias the foot pedal actuator 194, the linear optical encoder 202 is connected to a spring 206 which in turn is attached to the housing 196 by a securing pin 208. The spring 206 forces the vertical support member 200 into its most vertical positions when the foot pedal actuator 194 assembly is free standing. The foot pedal assembly 192 further includes two wheel members 211 and 213 which are located at the end of the linear optical encoder 202 opposing the spring 206. The wheel members 211 and 213 permit lateral movement of the linear optical encoder 202 when movement of the foot pedal actuator 194 cause the vertical support member 200 to displace the linear optical encoder 202.

To indicate the position of the linear optical encoder 202 when it is displaced by the vertical support member 200, a coupler 215 is provided which communicates with three optical transmitters 216, 218 and 220 and three optical receivers 222, 224 and 226. The optical transmitters 216, 218 and 220 communicate with the optical fibers 228, 230 and 232, while the optical receivers 222, 224 and 226 communicate with the optical fibers 234, 236 and 238. The coupler 215 includes a groove which is able to accommodate the linear optical encoder 202. To indicate when the foot pedal actuator 194 is in its upmost position, the linear optical encoder 202 includes an aperture 240. When the linear optical encoder 202 is disposed within the coupler 215 at a position which permits light to pass from the optical transmitter 220 through the aperture 240 to the optical receiver 226, an optical signal indicative of the upmost pedal position is delivered to the system console 12.

The location of the optical receivers 222 and 224 and transmitters 216 and 218 are staggered such that the optical fibers 234 receives a signal which is 90 degrees out of phase with the signal received by the optical fiber 236. The output from the optical fibers 234 and 236 can therefore be represented as a reflected or Gray code signal indicative of the linear displacement of the linear optical encoder 202 as described above. By recording the outputs delivered by the optical fibers 234 and 236, the linear position of the linear optical encoder 202 may be determined.

To secure the linear optical encoder 202 within the groove of the coupler 215, a spring member 239 is provided. The spring member 239 is secured to the optical coupler 215 through a post 240 and contains two bushings 242 and 244. The bushings 242 and 244 mechanically communicate with the linear optical encoder 202 thereby securing the linear optical encoder 202 within the groove of the coupler 215.

To permit lateral movement to actuate the foot pedal assembly 192, the foot pedal assembly 192 further includes two side actuators 246 and 248. The side actuators 246 and 248 are secured to the housing 196 by support members 250 and 252 which bias the side actuators 246 and 248 in a position adjacent to the stops 255 and 256. To optically encode the movement of the side actuator 248, the side actuator 248 mechanically communicates with a lever portion 258 of the side actuator switch 260. The side actuator switch 260 communicate with an optical transmitter 262 and an optical receiver 264 which in turn are connected to the optical fiber 266 and the optical fiber 268 respectively. When the actuator 248 is moved from its rest position against the stop 255, the lever portion 258 causes the side actuator switch 260 to optically couple the fiber 266 to the fiber 268, thereby producing an optical signal which is delivered to the console 12 through the fiber 268. To optically encode the movement of the side actuator 246, the side actuator 246 mechanically communicates with a lever portion 270 of a side activator switch 272. The side actuator switch 272 communicates with an optical transmitter 274 and an optical receiver 276 which are connected to respective optical fibers 278 and 280. Movement of the side actuator 272 from the stop 256 causes displacement of the lever portion 270 of the side actuator switch 272 thereby permitting optical coupling between the fiber 278 and the fiber 280. The optical fibers 278 and 280, as well as the optical fibers 228, 230, 232, 234, 236, 238, 266 and 268, are secured to the housing 196 by ties 282 and are secured to each other by the ties 284.

The foregoing discussion discloses and describes merely exemplary embodiments of the present invention. While the foot pedal assembly was described for use in controlling microsurgical instruments, the foot pedal assembly may be used in other appropriate applications. One skilled in the art will readily recognize from such discussion that various changes, modifications and variations may be made therein without departing from the spirit and scope of the invention as defined in the following claims. For example, while the foot pedal assemblies are shown to have optical fibers which bring light to the foot pedal assemblies, in the appropriate application, a light source could be contained within the foot pedal assemblies themselves, thereby eliminating the need for these particular optical fibers.

We claim:

1. A foot pedal assembly for remotely controlling an instrument, comprising:
   a base;
   a foot pedal movably mounted to said base; and
   means for providing an optically transmitted signal for controlling said instrument in response to the movement of said foot pedal with respect to said base;
   wherein said foot pedal is mounted for movement in a generally vertical direction, and said foot pedal assembly also includes two side actuators which are mounted to said base and associated with said signal providing means for providing a further optically transmitted signal for controlling said instrument, said side actuators being arranged so that said foot pedal is interposed between them.

2. The foot pedal assembly according to claim 1, wherein said optically transmitted signal comprises a plurality of individual light conveying channels.

3. The foot pedal assembly according to claim 2, wherein said signal providing means includes fiber optic conduit means for defining each of said light conveying channels and for transmitting light from said base through said plurality of light conveying channels.

4. The foot pedal assembly according to claim 3, wherein said fiber optic conduit means includes means for transmitting light both to and from said base through said plurality of light conveying channels.

5. The foot pedal assembly according to claim 2, wherein said signal providing means includes means for encoding the transmission of light on at least two of said light conveying channels.

6. The foot pedal assembly according to claim 5, wherein said encoding means is a rotating optical encoder which includes a generally flat disk that rotates in response to the movement of said foot pedal, said disk having a plurality of circumferentially spaced slots formed therein for selectively passing light through said disk.

7. The foot pedal assembly according to claim 4, wherein said two light conveying channels are associated with said disk such that a predetermined phase difference is provided between these two light conveying channels.

8. The foot pedal assembly according to claim 5, wherein said encoding means is a linear optical encoder which includes an elongated shutter member that slides in response to the movement of said foot pedal, said shutter member having a plurality of generally parallel slots formed therein for selectively passing light through said shutter member.

9. The foot pedal assembly according to claim 5, wherein said signal providing means includes optical switch means associated with one of said light conveying channels for providing an indication that said foot pedal is in a predetermined terminal position with respect to said base.

10. The foot pedal assembly according to claim 7, wherein said signal providing means includes a light conveying channel for each of said side actuators and optical switch means for each of said side actuators for controlling the transmission of light through said light conveying channels in response to the pivotal movement of each of these side actuators.

11. In a surgical system having a controller unit for controlling an ophthalmic surgical instrument, a foot pedal assembly for enabling remote control of said surgical instrument, comprising:
    a base;
    a foot pedal pivotally mounted to said base;
    means for conveying light between said base and said controller unit in a plurality of individual light conveying channels; and
    means for controlling the transmission of light to said controller unit from said base in response to the pivotal movement of said foot pedal such that an optical signal is provided from said base for remotely controlling said surgical instrument;
    wherein said foot pedal assembly also includes a pair of side actuators which are pivotally mounted to said base such that said foot pedal is interposed between them, and optical switch means for controlling the transmission of light to said controller unit from said base in response to the pivotal movement of said side actuators such that each of said side actuators provides an additional optical signal along one of said light conveying channels for controlling said surgical instrument.

12. The surgical system according to claim 11, wherein said means for controlling the transmission of light includes means for interrupting the transmission of light through at least two of said light conveying channels at predetermined pivotal positions of said foot pedal with respect to said base.

13. The surgical system according to claim 12, wherein said interrupting means includes an optical encoder.

14. The surgical system according to claim 12, wherein said interrupting means includes optical switch means for providing an optical signal along a third of said light conveying channels which indicates when said foot pedal is in a predetermined terminal position with respect to said base.

15. A foot pedal assembly for remotely controlling an instrument, comprising:
    a base;
    a foot pedal mounted on said base for pivotal movement about a generally horizontal axis;
    a pair of side actuators mounted on said base for pivotal movement about axes nonparallel to said generally horizontal axis;
    means for providing an optically transmitted signal for controlling said instrument in response to movement of said foot pedal and movement of said side actuators.

16. The foot pedal assembly of claim 15, wherein said foot pedal is interposed between said side actuators.

17. The foot pedal assembly of claim 15, wherein said optically transmitted signal comprises a plurality of individual light conveying channels.

18. The foot pedal assembly of claim 17, wherein said signal providing means includes fiber optic conduit means for defining each of said light conveying channels and for transmitting light from said base through said plurality of light conveying channels.

19. The foot pedal assembly of claim 18, wherein said fiber optic conduit means includes means for transmitting light both to and from said base through said plurality of light conveying channels.

20. The foot pedal assembly of claim 17, wherein said signal providing means includes means for encoding the transmission of light on at least two of said light conveying channels.

21. The foot pedal assembly of claim 20, wherein said encoding means is a rotating optical encoder which includes a generally flat disk that rotates in response to the movement of said foot pedal, said disk having a plurality of circumferentially spaced slots formed therein for selectively passing light through said disk.

22. The foot pedal assembly of claim 21, wherein said two light conveying channels are associated with said disk such that a predetermined phase difference is provided between these two light conveying channels.

23. The foot pedal assembly of claim 20, wherein said encoding means is a linear optical encoder which includes an elongated shutter member that slides in response to the movement of said foot pedal, said shutter member having a plurality of generally parallel slots formed therein for selectively passing light through said shutter member.

24. The foot pedal assembly of claim 20, wherein said signal providing means includes optical switch means associated with one of said light conveying channels for providing an indication that said foot pedal is in a predetermined terminal position with respect to said base.

25. The foot pedal assembly of claim 15, wherein said signal providing means includes a light conveying channel for each of said side actuators and optical switch means for each of said side actuators for controlling the transmission of light through said light conveying channels in response to the pivotal movement of each of these side actuators.

* * * * *

UNITED STATES PATENT AND TRADEMARK OFFICE
CERTIFICATE OF CORRECTION

PATENT NO. : 4,837,857

DATED : June 6, 1989

INVENTOR(S) : Gregg D. Scheller et al.

It is certified that error appears in the above-identified patent and that said Letters Patent is hereby corrected as shown below:

| | | |
|---|---|---|
| Column 1, | line 59, | delete "of" before --microsurgical--. |
| Column 1, | line 60, | insert "of" after --degree--. |
| Column 3, | line 19, | delete "operations" after --actuable--. |
| Column 4, | line 12, | "k21" should be --K21--. |
| Column 4, | line 13, | "k21" should be --K21--. |
| Column 5, | line 33, | "120" should be --102--. |
| Column 6, | line 3, | "the" should be --The--. |
| Column 8, | line 52, | "activator" should be --actuator--. |
| Column 9, | line 53, | dependent on "Claim 4" but should be dependent on --Claim 6--. |
| Column 10, | line 3, | dependent on "Claim 7" but should be dependent on --Claim 1--. |

Signed and Sealed this

Twenty-second Day of May, 1990

Attest:

HARRY F. MANBECK, JR.

*Attesting Officer*   *Commissioner of Patents and Trademarks*